United States Patent [19]

Irvine et al.

[11] Patent Number: 5,342,765
[45] Date of Patent: Aug. 30, 1994

[54] METHOD OF PRODUCING EXTRACELLULAR PRODUCTS FROM AEROBIC MICROORGANISMS

[75] Inventors: Robert L. Irvine, Notre Dame, Ind.; Rajagopalan Venkatadri, Argonne, Ill.

[73] Assignee: Occidental Chemical Corporation, Niagara Falls, N.Y.

[21] Appl. No.: 739,043

[22] Filed: Aug. 1, 1991

[51] Int. Cl.$^5$ .......................... C12P 21/04; C12P 1/02; C12N 11/08; C12N 9/08
[52] U.S. Cl. .................................... 435/71.1; 435/171; 435/180; 435/192; 435/288; 435/814
[58] Field of Search ............... 435/192, 183, 814, 288, 435/171, 180, 71.1

[56] References Cited

U.S. PATENT DOCUMENTS

| | | | |
|---|---|---|---|
| 4,554,075 | 11/1985 | Chang et al. | 210/611 |
| 4,749,654 | 6/1988 | Karrer et al. | 435/240.21 |
| 4,751,003 | 6/1988 | Raehse et al. | 435/814 |
| 4,925,803 | 5/1990 | Suehiro et al. | 435/288 |
| 4,999,298 | 3/1991 | Wolfe et al. | 435/240 |
| 5,153,121 | 10/1992 | Asther et al. | 435/71.1 |

OTHER PUBLICATIONS

Stanbury P. F. et al., Principles of Fermentation Technology, 1984, p. 173.
Barnett, S. M. et al., Fermentation & Enz. Sacchanfication of Cellulose and Lignin Waste, 1977, abstract.
Willershausen et al., *Biotechnology*, 6 (1987), pp. 239–243, "Ligninase Production Of Phanerochaete Chrysosporium by Immobilization in Bioreactors".
Aitken, Ph.D. Dissertation, Univ. Notre Dame (1988), pp. 82 to 122, "Studies On The Extracellular Peroxidase System of the White–rot *Fungas Phanerochaete chrysosporium*".
Jaar et al., "Biological Regeneration of Activated Carbon Loaded With 3 Chlorobenzoate," Z Wasser-Abwasser-Forsch 22(1), 1989.
Kirk et al., *Arch. Microbiol.* 117:277–285 (1978), "Influence of Culture Parameters on Lignin Metabolism by *Phanaerochaete Chrysosporium*".
Kniebusch et al., *Physiology of Immobilized Cells*, pp. 149–160, 1989, "Immobilization of Cells at Gas Permeable Membranes".

*Primary Examiner*—Douglas W. Robinson
*Assistant Examiner*—Deborah K. Ware
*Attorney, Agent, or Firm*—Wayne A. Jones; Richard D. Fuerle

[57] ABSTRACT

Disclosed is a method of producing an extracellular product from an aerobic microorganism. The microorganism is grown in an aqueous medium on one side of an oxygen-permeable surface while the opposite side of the surface is contacted with oxygen. The extracellular product is then harvested from the aqueous medium. The method is particularly useful in producing lignin peroxidase from the white rot fungus *Phanerochaete chrysosporium*.

10 Claims, 2 Drawing Sheets

METHOD OF PRODUCING EXTRACELLULAR PRODUCTS FROM AEROBIC MICROORGANISMS

BACKGROUND OF THE INVENTION

This invention relates to a method of producing extracellular products from aerobic microorganisms. In particular, it relates to a method wherein an aerobic microorganism is grown in an aqueous medium on one side of an oxygen-permeable surface while the opposite side of the surface is contacted with oxygen, and an extracellular product is harvested from the aqueous medium.

Lignin is the major non-carbohydrate constituent of wood and woody plants and functions as a natural plastic binder for cellulose fibers. Organisms, such as fungi, that feed on cellulose produce a peroxidase called "lignin peroxidase" which attacks and degrades lignin, thereby giving the organism access to the cellulose. Peroxidases, in general, are enzymes that utilize hydrogen peroxide as a co-substrate in reactions that involve one electron transfer and are useful in a variety of chemical processes, including catalysis reactions in the production of pharmaceuticals, enzyme catalyzed analytical reactions, and the degradation of toxic organic waste products. At the present time, peroxidase can be obtained from horseradish or from fungi that naturally produce it. Most processes for obtaining lignin peroxidase from fungi involved agitation in a large reactor with a growth medium and it has been shown (see Venkatadri, R. and Irvine, R. L., "Effect of Agitation on Ligninase Activity and Ligninase Production by *Phanerochaete chrysosporium,*" *Applied and Environmental Microbiology,* 56, 2684–2691, 1990) that the presence of a surfactant is required to prevent the agitation from inactivating the enzyme. The current method of obtaining lignin peroxidase is costly and, as a result, the price of lignin peroxidase is relatively high.

SUMMARY OF THE INVENTION

We have discovered a superior method of producing extracellular products from aerobic microorganisms, particularly for producing lignin peroxidase from a white rot fungus. In the method of this invention, a microorganism is grown on one side of an oxygen-permeable surface in an aqueous medium while the opposite side of the surface is supplied with oxygen. We have found that by immobilizing the organism on an oxygen-permeable surface and by supplying oxygen to the organism through the oxygen-permeable surface, the production of the extracellular enzyme by the microorganism developed to a level of 230 units/L (U/L) and averaged 121 U/L over 8 batch production periods. When the organism was suspended and air or oxygen supply to the organism was provided by being bubbled through the aqueous medium, only one production of 25 U/L lignin peroxidase activity was obtained. When the organisms were attached to an oxygen permeable membrane but oxygen was supplied by flushing oxygen through the headspace of the reactor and not through the membrane, no enzyme activity was observed after the initial addition of production medium. After the medium was replaced with a second production medium, enzyme activity developed to a maximum level of 92 U/L and no further enzyme activity was observed after production medium was added two additional times.

DESCRIPTION OF THE INVENTION

Figure 2:
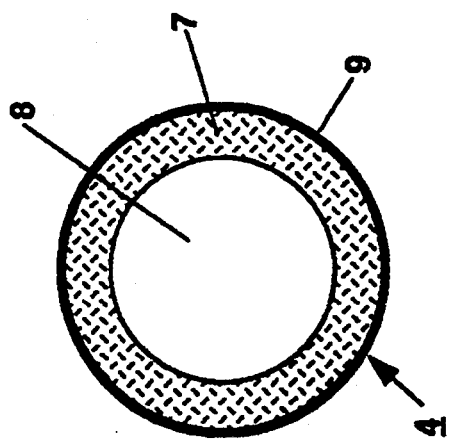
FIG. 2 is a cross section of the oxygen-permeable tubing shown in FIG. 1.
Figure 1:
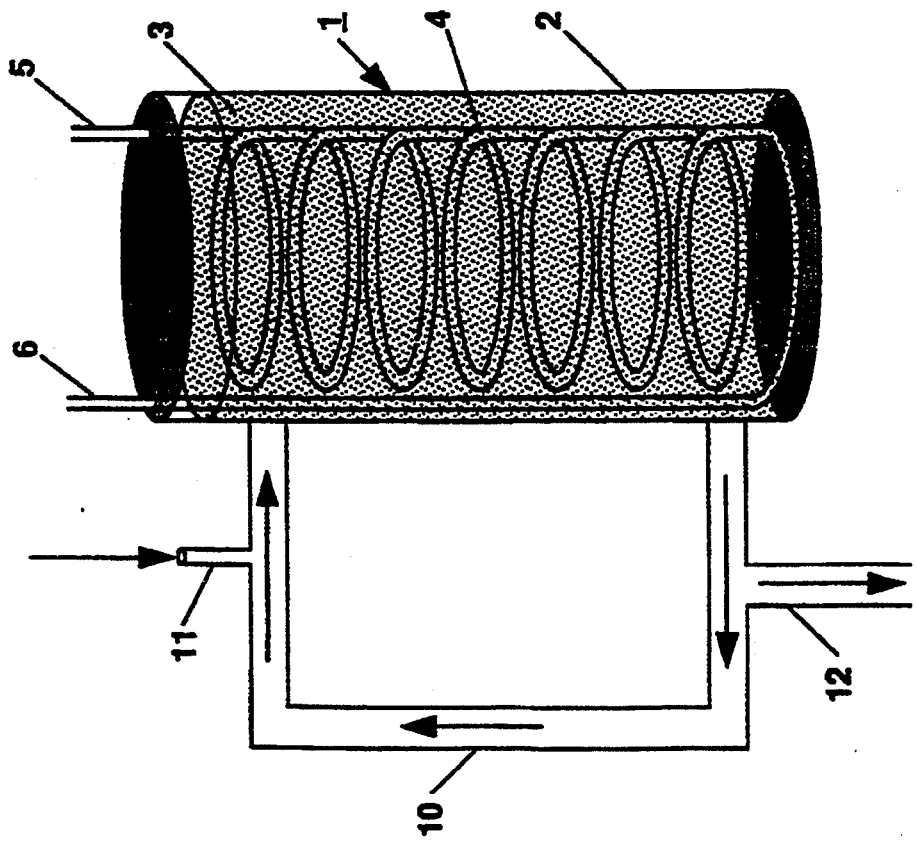
FIG. 1 is a diagrammatic view of a certain presently preferred embodiment of apparatus that illustrate the process of this invention.

In FIG. 1, a reactor 1 consists of a tank 2 containing an aqueous medium 3 in which is immersed tubing 4 having an inlet 5 and an exhaust 6. Referring to FIG. 2, tubing 4 is made of an oxygen-permeable material 7. An oxygen-containing gas flows through lumen 8 and a film 9 of an aerobic microorganism grows on the outside of tube. Referring to FIG. 1 again, aqueous medium is recirculated through reactor 1 through loop 10. Nutrients are supplied into the loop through input 11 and the enzyme product is removed through outlet 12.

The method of this invention is applicable to any aerobic microorganism, including, for example, bacteria, fungi, yeast, and animal cells such as mammalian cells. Examples of fungi that can be used in the process of this invention include the white rot fungus, (*Phanerochaete chrysosporium*), which produces lignin peroxidase, and other peroxidase producing fungi including, *Coprinus cinerus* (macrorhizus), *Arthromyces ramosus,* and *Caldariomyces fumago.* The process of this invention can be used to make a variety of extracellular products including, for example, various enzymes, antibiotics, alcohols, pharmaceuticals, hormones, and proteins. Examples of enzymes that can be produced include the peroxidases, particularly the many lignin peroxidases that can be produced by the various fungi that are referred to broadly as the white rot fungus.

The oxygen-permeable membrane used in the process of this invention can be made of a variety of oxygen-permeable synthetic resins including, for example, silicone rubber, polysiloxanes, and polyimidesiloxanes. The membrane can be in the form of a flat surface, a bag, a tube, or other shapes. Tubes are preferred as they are the easiest to keep clean and to work with, and are convenient for scale up. If the gas supplied to the tube is not pure oxygen it is usually necessary to use a tube that has both an inlet and an outlet, but if pure oxygen is used no outlet is necessary. Also, if the product being produced by the process of this invention is volatile and can pass through the permeable membrane, it is preferable to use tubing that does not have an outlet to prevent loss of the volatile material through the membrane.

In the process of this invention, the microorganism to be grown is placed in an aqueous medium that contains nutrients appropriate for stimulating the growth of the microorganism. The aqueous medium is placed on one side of the oxygen-permeable membrane and an oxygen-containing gas is placed on the other side. While some organisms will produce the desired product during growth, for many organisms it is necessary to stress the organism in order to stimulate the production of the desired product. Typically this is accomplished by reducing the supply of nutrients to the organism. In the case of white rot fungus, for example, when the nutrient supply is reduced and the fungus begins to starve, it initiates the production of lignin peroxidase from some of its own protoplasm. After a period of lignin peroxidase production, it is necessary to again feed the fungus and stimulate its growth. Thus, production typically proceeds through alternating cycles of growth and peroxidase production which are controlled by supplying the fungus with a growth-producing medium followed by an enzyme-producing medium which is deficient in certain nutrients. After a number of cycles, the microorganism may begin to show signs of exhaustion and its rate of enzyme production may fall. Rejuvenation of the microorganism can be accomplished by, for example, hosing down the membrane to remove older fungi and permit the growth of the younger fungi. Other methods of rejuvenating the microorganism may also be appropriate.

The following examples further illustrate this invention.

EXAMPLE 1

*Phanerochaete chrysosporium* VKM F-1767 (ATCC 24725) is publicly available from American Type Culture Collection, 12301 Parklawn Drive, Rockville, Md. 20852. A sample of the fungus, obtained from that source, was cultured at 37° C. in a batch/continuous reactor Bioflow II (New Brunswick Scientific Co., N.J.). The reactor was equipped with built-in control for pH, dissolved oxygen, agitation and temperature. The reactor vessel was 2.5-L thick-walled, flanged tube anchored to a stainless steel headplate and a bottom-dished head which was jacketed for the circulation of water.

The reactor was modified for the growth of *P. chrysosporium* as a biofilm attached to a semipermeable silicone rubber membrane tubing. Fifteen feet of silicone tubing (⅛ in. i.d., 3/16 in o.d., 1/32 in. wall, Cole-Parmer) was wrapped in a mesh around five stainless steel rods (¼ in. ×14 in.) inserted through the headplate of the bioreactor. The rods were arranged along the circumference of the reactor. The mesh of silicone tubing was fully submerged in 1.5 L of growth medium (see Table 1), and acted as a solid support for the growth of *P. chrysosporium*. The medium was periodically replaced with growth and production media (Table 1) as described hereinbelow. Veratryl alcohol (1 mM) was used along with the production medium to enhance lignin peroxidase production.

The silicone tubing also acted as an oxygen supply source for the organism's oxygen requirement. Air, at 5 psi, was pumped through one end of the silicone tubing mesh with the other end of the tubing being sealed. This forced gas to transfer across the walls of the tubing and into the cells immobilized on the outside wall of the tubing and into the bulk liquid phase. Oxygen, at 5 psi, was used instead of air during the enzyme production periods (secondary metabolic phases). Using air addition, the dissolved oxygen concentration in the reactor fluid was maintained at around 60% of air saturation and, using oxygen, the dissolved oxygen was maintained at supersaturated concentrations. Oxygen delivery through the silicone tubing was shown to be critical to the process since, in Example 2 (in which oxygen was supplied by flushing the headspace), lignin peroxidase production was dramatically reduced and production was limited to the second cycle.

Inoculation was by the addition of a spore suspension (final concentration $4 \times 10^3$) to the reactor fluid. Prior to inoculation, the reactor was purged with nitrogen gas, using the silicone tubing for gas transfer, to lower the dissolved oxygen levels in the bulk liquid phase. This was done in order to facilitate attached growth on the silicone tubing (after air addition was started) and prevent growth on the walls of the reactor. Mixing was accomplished using a turbine-blade impeller (40 rpm during the growth phase and 25 rpm during the production phase).

Following inoculation of the reactor, *P. chrysosporium* was observed to grow as a film on the mesh of silicone tubing. Growth was accompanied by the consumption of glucose. It took three days for the glucose concentration to decrease from 2 g/L to 1 g/L. The silicone tubing appeared to be an excellent support for the attached growth of the fungus with minimal growth on the walls of the reactor. Also, the reactor fluid was clear with the absence of any unattached fungal mycelia.

Figure 3:
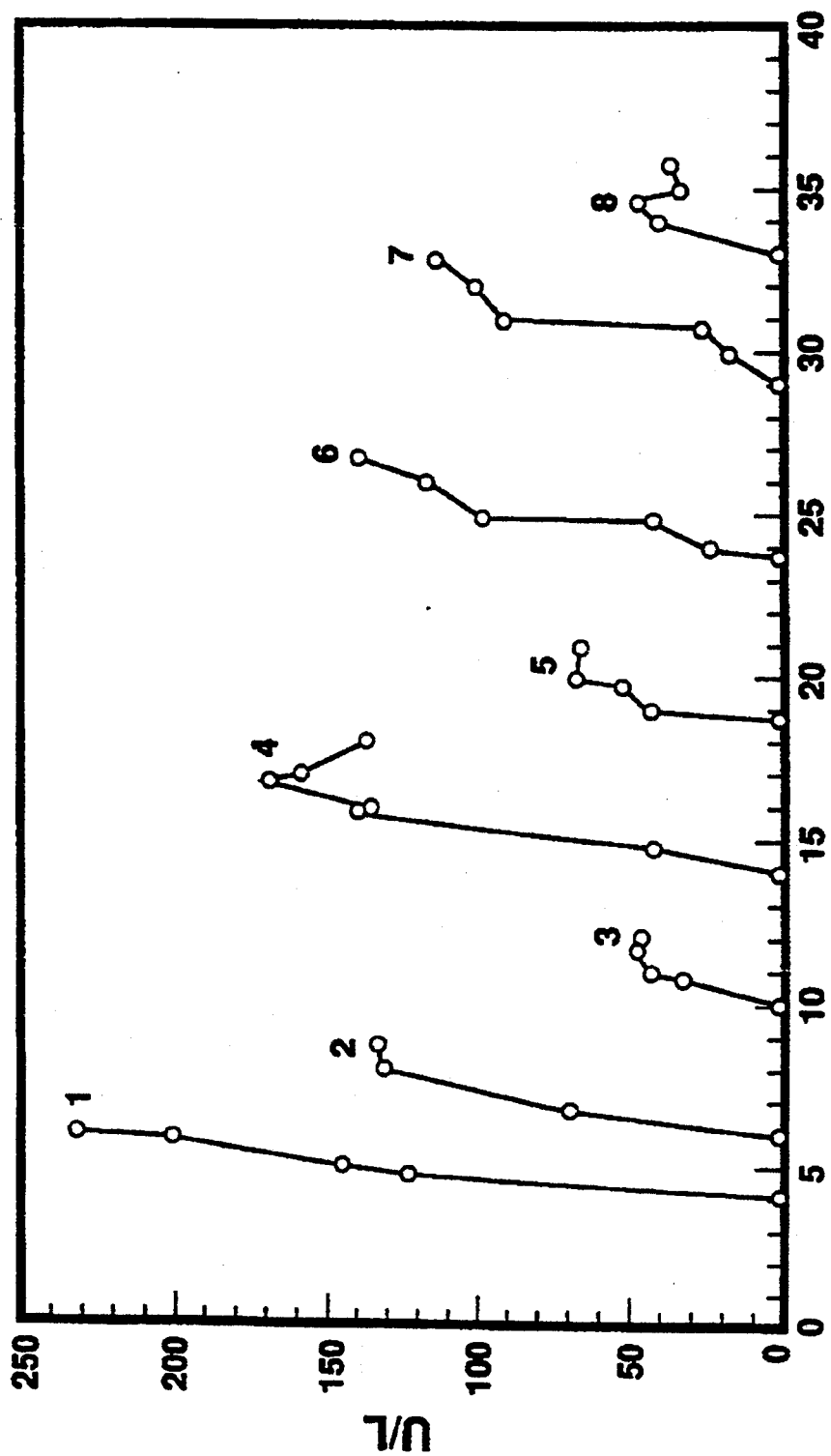
FIG. 3 is a graph giving the results of experiments described in Example 1.

Following three days of growth, the growth medium in the reactor was replaced with the production medium and veratryl alcohol (1 mM) which resulted in the appearance of lignin peroxidase activity in the reactor fluid (Table 2). In FIG. 3, the ordinate is lignin peroxidase activity in units per liter and the abscissa is the age of the culture in days. Enzyme activity developed to a level of 230 units/L (U/L) after which the medium was replaced with a second production medium and veratryl alcohol (1 mM). A maximum activity of 135 U/L was obtained in the second production medium.

The reactor was then operated using a strategy in which the organism was subject to alternating periods of growth and secondary metabolism by periodic replacements of growth and production media. The schedule of events in the operation of the reactor is detailed in Table 2. The use of this strategy resulted in the semi-continuous production of lignin peroxidase. An average lignin peroxidase activity of 121 U/L was obtained in 8 batches of 1.5 L each. By way of comparison, only 25 U/L lignin peroxidase activity was obtained with a suspended growth system with air or oxygen being bubbled through the medium.

To show that this process is applicable to other fungi, experiments were performed to demonstrate production of an extracellular peroxidase from the marine fungus *Caldariomyces fumago* (ATCC 16373, also publicly available from American Type Culture Collection, 12301 Parklawn Drive, Rockville, Md. 20852) and a laccase from *Trametes versicolor*. Enzymes were expressed by both fungi. In the case of *C. fumago*, the growth medium described by Hollenberg and Hager (1978) Method in Enzymology 52:521–529 was used whereas in cultures of *T. versicolor*, (publicly available from the U.S. Department of Agriculture, Forest Products Laboratory, Madison, Wis. 53705) the medium described by Fahraeus and Reinhammar (1967) Acta Chemica Scandinavica 21:2367–2378 was used. In both cases, cultures were initiated with a mycelial suspension and were incubated at room temperature.

TABLE 1

Composition of Media used in Cultivation of *P. chrysosporium*

| Component | Concentration | |
|---|---|---|
| | Growth medium | Production medium |
| Glucose | 11.1 mM | — |
| 2,2-Dimethylsuccinic acid | 15 mM | 10 mM |
| Thiamine.HCl | 0.17 μM | 0.02 μM |
| L-Asparagine | 1 mM | 1 mM |
| Nitrilotriacetic acid | 53 μM | 200 μM |
| Potassium gluconate | — | 5 mM |

TABLE 1-continued

Composition of Media used in Cultivation of *P. chrysosporium*

| Component | Concentration Growth medium | Production medium |
|---|---|---|
| $NH_4Cl$ | 5.9 mM | — |
| $KH_2PO_4$ | 1.5 mM | 1.5 mM |
| $MgSO_4$ | 0.2 mM | 0.2 mM |
| $CaCl_2$ | 0.1 mM | 0.1 mM |
| $MnSO_4$ | 5 μM | 100 μM |
| $FeCl_3$ | 5 μM | 5 μM |
| $CuSO_4$ | 0.17 μM | 0.17 μM |
| $NH_4HCO_3$ | 0.2 mM | — |
| $CoCl_2$ | 0.33 μM | 0.33 μM |
| $ZnSO_4$ | 0.83 μM | 0.83 μM |
| $H_3BO_3$ | 0.27 μM | 0.27 μM |
| $AlK(SO_4)_2$ | 0.04 μM | 0.04 μM |
| $NH_4MoO_4$ | 0.1 μM | 0.1 μM |
| pH | 4.5 | 4.5 |

TABLE 2

Schedule of Events in the Operation of the Biofilm Reactor

| Day | Event |
|---|---|
| 0 | Inoculated reactor |
| 3 | Replaced growth medium with production medium and veratryl alcohol (1 mM) |
| 6 | Replaced with production medium and veratryl alcohol (1 mM) |
| 9 | Replaced with growth medium containing 0.2 g/L glucose |
| 10 | Added veratryl alcohol (1 mM) |
| 12 | Replaced with growth medium containing 0.4 g/L glucose |
| 13 | Added 0.463 g/L glucose by spiking |
| 14 | Replaced with production medium and veratryl alcohol (1 mM) |
| 18 | Replaced with production medium and veratryl alcohol (1 mM) |
| 21 | Replaced with growth medium containing 0.8 g/L glucose |
| 23 | Replaced with production medium and veratryl alcohol (1 mM) |
| 27 | Harvested medium, removed part of the biomass and replaced with growth medium containing 1 g/L glucose |
| 29 | Replaced with production medium and veratryl alcohol (1 mM) |
| 33 | Replaced with production medium and veratryl alcohol (1 mM) |

Example 2

Example 1 was repeated except that no oxygen or air was supplied to the inside of the tubing. The same length of silicone tubing was added to the reactor but the ends were clamped off so that it would not serve as a source of oxygen. Instead, oxygen was supplied by flushing oxygen through the headspace of the reactor. Under these conditions, fungal growth was not restricted to the surface of the silicone tubing and excessive growth occurred through the reactor and impaired operation. No enzyme activity was observed after the initial addition of production medium. After the medium was replaced with a second production medium, enzyme activity developed to a maximum level of 92 U/L and no further enzyme activity was observed after production medium was added two additional times.

We claim:

1. A method of producing a peroxidase comprising
   (1) growing an aerobic fungus that produces a peroxidase extracellularly on the outside of an oxygen-permeable tubing, in an aqueous medium containing growth-stimulating nutrients;
   (2) maintaining an oxygen-containing gas in said tubing;
   (3) stimulating the repeated production of said peroxidase by alternatively providing and reducing the amount of said nutrients supplied to said fungus; and
   (4) collecting said peroxidase from said aqueous medium.

2. A method according to claim 1 wherein said peroxidase is lignin peroxidase.

3. A method according to claim 1 wherein said fungus is a white rot fungus.

4. A method according to claim 3 wherein said white rot fungus is *Phanerochaete chrysosporium*.

5. A method according to claim 1 wherein said fungus is *Trametes versicolor*.

6. A method according to claim 1 wherein said fungus is *Caldariomyces fumago*.

7. A method of producing lignin peroxidase comprising
   (1) growing *Phanerochaete chrysosporium* in an aqueous medium on the outside of oxygen-permeable tubing;
   (2) maintaining a source of oxygen inside said tubing;
   (3) alternately supplying said *Phanerochaete chrysosporium* with nutrients to stimulate growth and starving said *Phanerochaete chrysosporium* to stimulate the production of said lignin peroxidase; and
   (4) collecting said lignin peroxidase from said aqueous medium.

8. A method according to claim 7 wherein said oxygen-permeable tubing is made of silicone rubber.

9. A method according to claim 7 wherein said *Phanerochaete chrysosporium* is ATCC 24725.

10. A method according to claim 7 wherein said aqueous medium contains veratryl alcohol.

* * * * *